United States Patent
Cox et al.

(10) Patent No.: US 6,579,310 B1
(45) Date of Patent: Jun. 17, 2003

(54) STENT HAVING OVERLAPPING STRUTS

(75) Inventors: Daniel L. Cox, Palo Alto, CA (US); Kenny Dang, San Jose, CA (US); Andreina P. Gomez, Palo Alto, CA (US); Orlando Padilla, Los Gatos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 168 days.

(21) Appl. No.: 09/641,984

(22) Filed: Aug. 17, 2000

(65) Prior Publication Data (65)

(51) Int. Cl.⁷ .................................................. A61F 2/06
(52) U.S. Cl. ..................................... 623/1.16; 623/1.15
(58) Field of Search ............................. 623/1.15, 1.16, 623/1.1, 1.18, 1.2; 606/191, 192, 194, 195, 198

(56) References Cited

U.S. PATENT DOCUMENTS

| | | |
|---|---|---|
| 3,657,744 A | 4/1972 | Ersek |
| 4,553,545 A | 11/1985 | Maass et al. |
| 4,649,922 A | 3/1987 | Wiktor |
| 4,655,771 A | 4/1987 | Wallsten |
| 4,681,110 A | 7/1987 | Wiktor |
| 4,733,665 A | 3/1988 | Palmaz |
| 4,740,207 A | 4/1988 | Kreamer |
| 4,762,128 A | 8/1988 | Rosenbluth |
| 4,830,003 A | 5/1989 | Wolff et al. |
| 4,848,343 A | 7/1989 | Wallsten et al. |
| 4,886,062 A | 12/1989 | Wiktor |
| 4,994,071 A | 2/1991 | MacGregor |
| 5,015,253 A | 5/1991 | MacGregor |
| 5,019,090 A | 5/1991 | Pinchuk |
| 5,061,275 A | 10/1991 | Wallsten et al. |
| 5,092,877 A | 3/1992 | Pinchuk |
| 5,104,404 A | 4/1992 | Wolff |
| 5,133,732 A | 7/1992 | Wiktor |
| 5,171,262 A | 12/1992 | MacGregor |
| 5,618,299 A * | 4/1997 | Khosravi et al. ............ 623/1.2 |
| 5,911,752 A * | 6/1999 | Dustrude et al. ........ 604/96.01 |
| 6,224,626 B1 * | 5/2001 | Steinke ...................... 623/1.16 |
| 6,340,366 B2 * | 1/2002 | Wijay ....................... 623/1.13 |

FOREIGN PATENT DOCUMENTS

WO    WO 99/65421    12/1999

OTHER PUBLICATIONS

Dotter, Charles T., et al., *Transluminal Expandable Nitinol Coil Stent Grafting: Preliminary Report*, Radiology Journal, pp. 259–260, Apr. 1983.

Cragg, Andrew, et al., *Non–Surgical Placement of arterial Endoprostheses: A New Technique Using Nitinol Wire*, Radiology Journal, pp. 261–263, Apr. 1983.

* cited by examiner

Primary Examiner—David J. Isabella
Assistant Examiner—Urmi Chattopadhyay
(74) Attorney, Agent, or Firm—Fulwider Patton Lee & Utecht, LLP

(57) ABSTRACT

An intravascular stent having struts which overlap, at least partially, when the stent is compressed. The overlapping struts allow the stent to be crimped to a smaller initial delivery diameter than may be achieved with non-overlapping designs for given metal density. The stent has a reduced delivery diameter which allows for the construction of reduced profile stent-delivery systems, which thereby allow for the stenting of smaller vessels than has heretofore been possible.

33 Claims, 10 Drawing Sheets

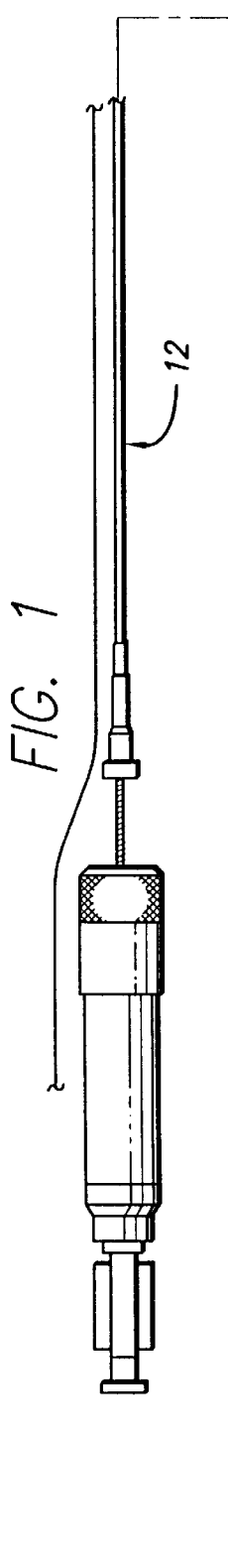
FIG. 1
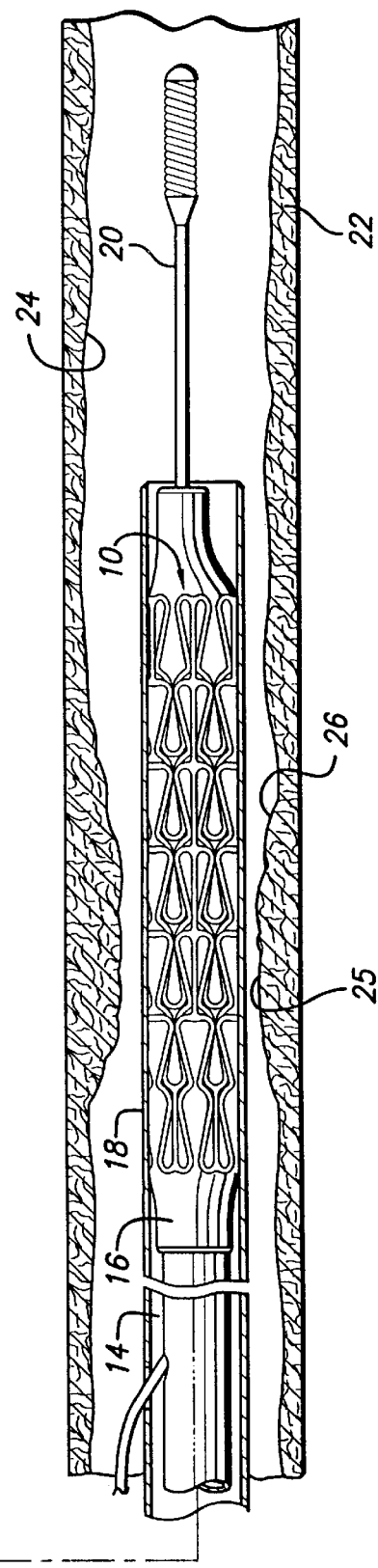
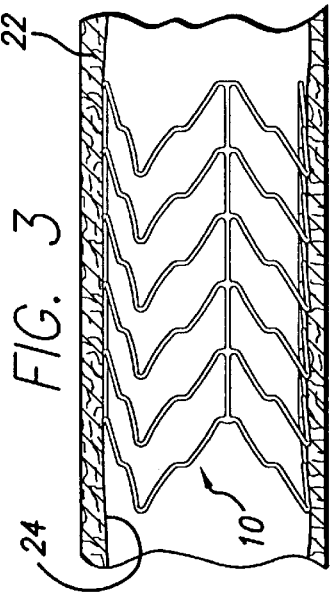
FIG. 3
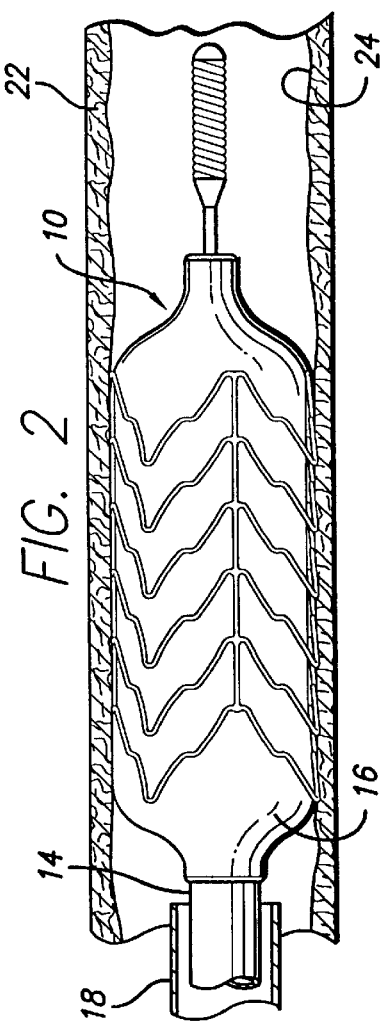
FIG. 2

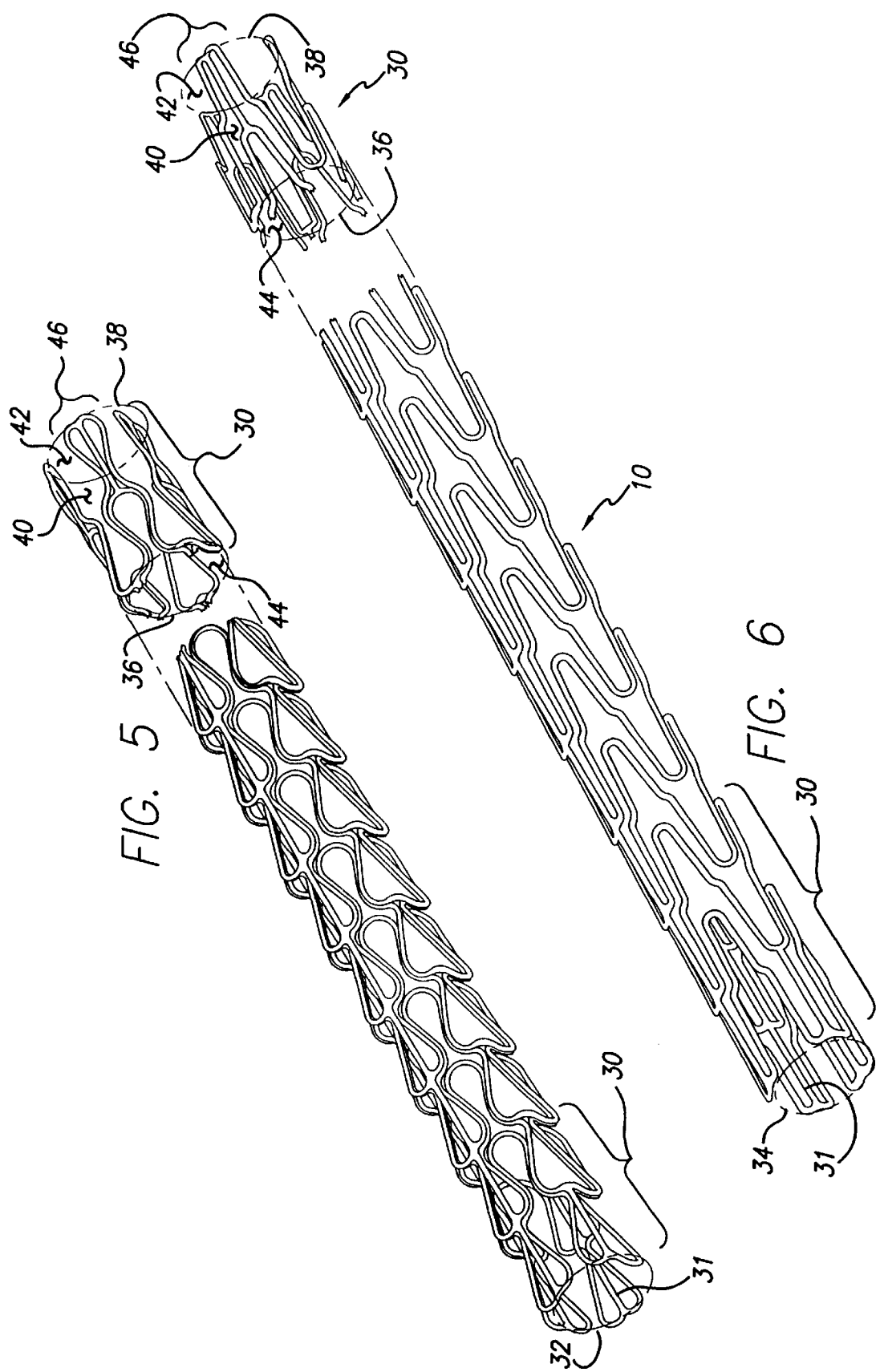

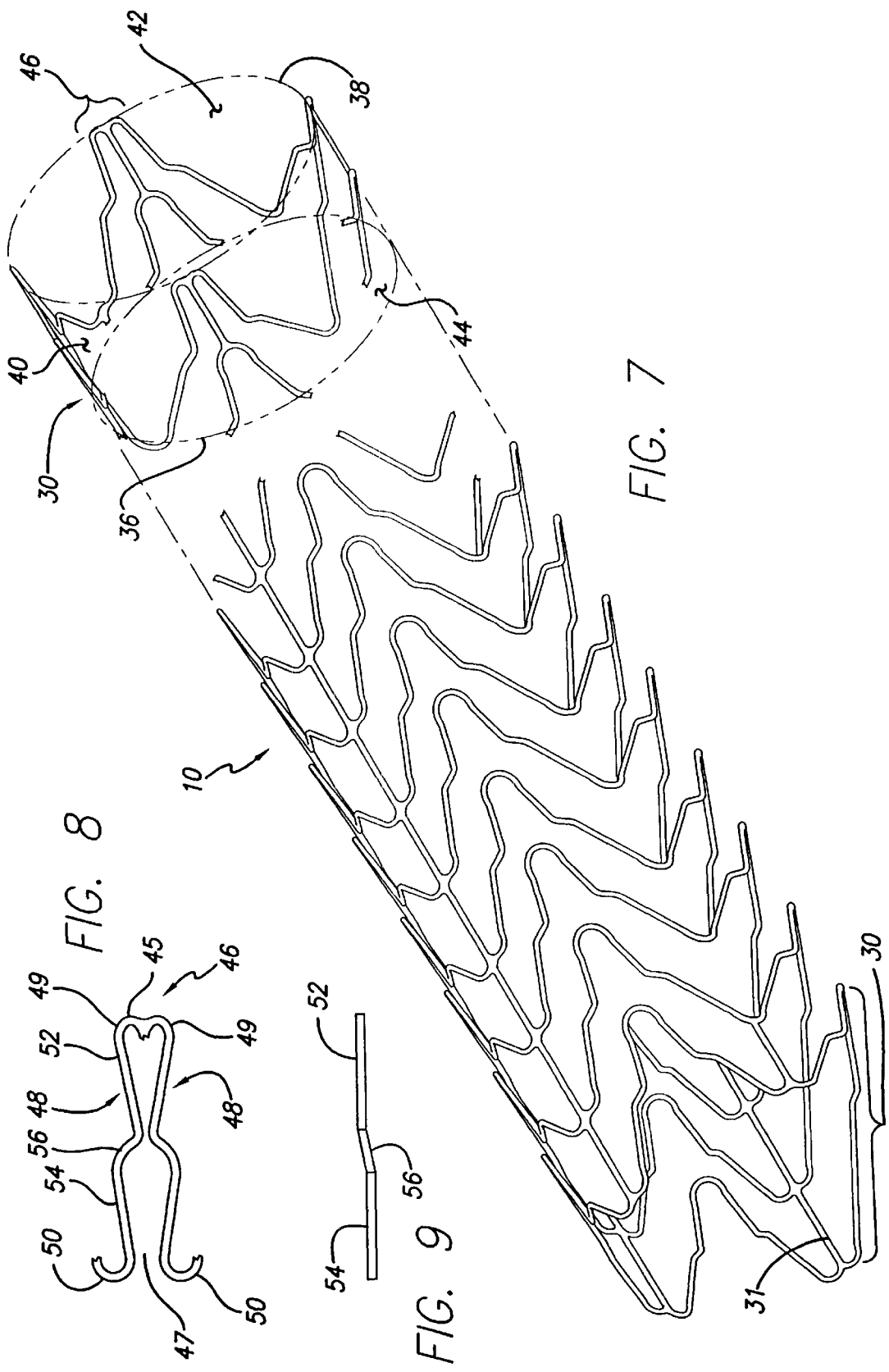

STENT HAVING OVERLAPPING STRUTS

BACKGROUND OF THE INVENTION

The present invention relates generally to endoprosthesis devices, which are commonly referred to as stents, and more particularly pertains to improvements thereto that provide for a reduced delivery profile, increased vessel scaffolding and in the case of balloon expandable stents, improved stent security.

Stents are generally thin walled tubular-shaped devices composed of complex patterns of interconnecting struts which function to hold open a segment of a blood vessel or other body lumen such as a coronary artery. They also are suitable for supporting a dissected arterial lining or intimal flap that can occlude a vessel lumen. There are two general classes of stents, balloon expandable stents and spring-like self-expandable stents. Balloon expandable stents are delivered within a vessel lumen by means of a dilatation catheter and are plastically deformed by means of an expandable member, such as an inflation balloon, from a small initial diameter to a larger expanded diameter. Self-expanding stents by contrast are formed as spring elements which are radially compressible about a delivery catheter. A compressed self-expanding stent is typically held in the compressed state by a delivery sheath. Upon delivery to a lesion site, the delivery sheath is retracted allowing the stent to expand.

Either type of stent has advantages and disadvantages. One disadvantage of self expanding stents with respect to balloon expandable stents is the relatively large profile of the self-expanding stent-delivery system. Because, self-expanding stents typically are restrained during delivery by a sheath, the outside diameter of a self-expanding stent-delivery system is greater than that of a comparable balloon expandable stent-delivery system which does not require a delivery sheath. As such, balloon expandable stents may be delivered within smaller vessels than can now be reached with a self-expanding stent.

One disadvantage of balloon expandable stents is the tendency for the stent to slip on the inflation balloon. Balloon expandable stents are typically crimped onto an inflation balloon in such a manner as to provide for a uniform crimp of the stent about the balloon. Typically, such crimps adequately secure the stent to the balloon. However, in certain circumstances, such as when the stent encounters obstacles such as hardened plaque or a flap of tissue partially torn from a vessel wall, stents occasionally slide off of the delivery catheter. It is believed that this slippage problem occurs because the stent forms a smooth continuous interface with the balloon and may not always generate sufficient frictional resistance to remain positioned on the balloon when encountering obstacles within the patient's vasculature. One approach to solving the slippage problem is to protect the balloon expandable stent with a delivery sheath. However, the use of a delivery sheath negates the reduced profile advantage of balloon expandable stent-delivery systems with respect to self-expanding stent-delivery systems.

Both balloon expandable and self-expandable stents must be able to simultaneously satisfy a number of interrelated mechanical requirements. First, the stent must exhibit sufficient radial or hoop strength in its expanded state to withstand the structural loads, namely radially compressive forces, imposed on the stent by the walls of a vessel. It is advantageous to distribute such loads over as much of the stent as possible and over as much lumen wall as possible. Uniform loading minimizes the possibility of localized crippling of the stent which may induce a general structural failure. In addition, uniform loading tends to minimize injury to the vessel wall. Second, it is desirable for a stent to provide a high degree of scaffolding of the lumen walls, i.e., minimize the gaps between stent struts, in order to prevent prolapse of plaque between the struts and into the lumen. Third, a stent should be sufficiently radiopaque to be readily visible by fluoroscopy procedures. Radiopacity with typical stent materials such as stainless steel and nickel-titanium alloy is generally a function of the stent's mass, and is in particular a function of the thickness of the stent struts. Fourth, a stent should be longitudinally flexible in order to be delivered through tortuous vessels. Finally, a stent should have a small crimped or initial delivery diameter in order to facilitate advancement through small vessels and must be able to expand to a second larger diameter for implantation within a body lumen. Generally, stents with large expansion ratios are preferred.

A number of approaches have been devised in an effort to address these various requirements. A popular early approach called for the stent to be constructed wholly of wire. The wire is bent, woven and/or coiled to define a generally cylindrical structure in a configuration that has the ability to undergo radial expansion. Wire stents have a number of disadvantages including for example, a substantially constant cross-section which may cause greater or lesser than an ideal amount of material to be concentrated at certain locations along the stent. Wire also has limitations with respect to the shapes into which it may be formed, thus limiting the expansion ratio, coverage area, and strength that can ultimately be attained.

More recent stents have been constructed from drawn tubing. By selectively removing material from tube stock, a stent with complex patterns of interconnecting struts may be formed. At present, there are numerous commercial tube based stents with a variety of strut geometries being marketed throughout the world. Whether a stent is self-expanding or balloon expandable is primarily a function of the stent's material. Balloon expandable stents and self-expanding stents may have the same geometric pattern with the determining factor being the use of a spring-like or shape memory material for a self-expanding version of the stent or the use of a plastically deformable material for a balloon expandable version of the stent. The selection of a particular pattern has a profound effect on the radial strength, scaffolding, radiopacity, and initial or crimped profile of the resulting stent.

While tube-based stents offer many advantages over the early wire-based designs, there remains room for improvement in the art. In particular, there is a need to reduce the delivery profile of stents, particularly with regard to self-expanding stents, and to increase the security of balloon expandable stents on the inflation balloon. The present invention meets these and other needs.

SUMMARY OF THE INVENTION

The present invention provides a stent which may be crimped to a smaller delivery diameter than previously known stent devices for a given metal density. In addition, the stent may positively engage the material of an inflation balloon, in a manner previously thought undesirable in the art, and thereby improve stent security on the balloon. The stent achieves these results while continuing to fulfill all of the mechanical and structural requirements attendant to its function as a stent.

The stent of the present invention can take many forms and preferably is configured to form a tubular member having a lattice structure of struts. The stent has a smaller delivery diameter in which it is preferably mounted on a catheter, and an expanded diameter wherein it is implanted in a body lumen, such as a coronary artery. When the stent is in the smaller delivery diameter, at least some of the struts overlap so that the stent has a very small profile, increased gripping force on the catheter, and is able to achieve a larger expanded diameter. The struts can overlap circumferentially or along the longitudinal axis of the stent, or both.

In one embodiment, the stent of the present invention includes generally a plurality of cylindrical rings that are interconnected by a plurality of links. When viewed in isolation, each cylindrical ring is generally formed as a pattern of alternating U-shaped portions which may be thought of as comprising a plurality of peaks and valleys, where a peak represents the apex of the U-shaped portion and a valley represents the space between the struts which form the open end of the U. The stent's advantages are achieved by circumferentially offsetting the valleys of each cylindrical ring from those of adjacent cylindrical rings and by nesting the rings such that the peaks of each adjacent cylindrical ring are centered midway within the valleys of each preceding ring. The U-shaped portions are formed from struts which are configured with an angled step midway along their length. The angled step essentially divides each strut into an upper portion and a lower portion. Thus, when the stent is crimped or compressed to its initial delivery diameter, the lower portion of each strut slides underneath the upper portion of each strut in a preceding nested ring. Thus, when compressed, the stent forms a pattern of nested cylindrical rings with overlapping struts. The overlapping struts allow the stent to be crimped to an initial delivery diameter smaller than that of prior art non-overlapping strut designs for a given metal density. Therefore, the profiles of both balloon expandable and self-expandable stent-delivery systems may be reduced with the present invention stent. Reduced delivery system profiles allow smaller vessels to be treated with the present invention stent than can be reached with prior art stents. In addition, in balloon expandable embodiments of the stent, the overlapping strut configuration allows the struts to engage or pinch the balloon material, thereby increasing stent security on the balloon.

Each of the cylindrical rings making up the stent has a proximal ed and a distal end and a cylindrical plane defined by a cylindrical outer wall surface that extends circumferentially between the proximal end and the distal end of the cylindrical ring. The cylindrical rings are interconnected by at least one longitudinal connecting link which attaches one cylindrical ring to an adjacent cylindrical ring. In addition, each connecting link may be circumferentially offset from the previous connecting link in a preceding ring. Circumferentially offsetting the links increases the longitudinal flexibility of the stent. The connecting links are positioned substantially within the cylindrical plane of the outer wall surface of the cylindrical rings.

Each connecting link is about one half the length of the struts which form each U-shaped portion. The connecting links are positioned so that they are within the curved part of a U-shaped portion and connect the apex of one U-shaped portion to the apex of a preceding U-shaped portion, positioning the preceding U-shaped portion about half way within the valley of the succeeding U-shaped portion. Typically, balloon expandable embodiments of the stent may be formed from a plastically deformable metal alloy such as stainless steel and similar materials. Self-expanding embodiments may be formed from shape memory alloys or superelastic alloys which expand upon undergoing a martensite to austenite phase change. Such a phase change is typically initiated by increasing the temperature of the alloy above a predetermined transition temperature, or in the case of alloys which exhibit stress induced martensite phase changes, upon relieving an imposed stress.

The stent may be formed from a tube by laser cutting the pattern of cylindrical rings and connecting links in the tube. The stent also may be formed by laser cutting a flat metal sheet in the form of the cylindrical rings and links, and then rolling the pattern into the shape of the cylindrical stent and providing a longitudinal weld to form the stent.

These and other features and advantages of the present invention will become apparent from the following detailed description, which when taken in conjunction with the accompanying drawings, illustrate by way of example the principles of the invention.

BRIEF DESCRIPTION OF THE DRAWINGS

FIG. 1 is an elevational view, partially in section, of a stent embodying features of the invention and which is mounted on a balloon dilatation catheter and disposed within an artery.

FIG. 2 is an elevational view, partially in section, similar to that shown in FIG. 1 wherein the stent is expanded within the artery, so that the stent embeds within the arterial wall.

FIG. 3 is an elevational view, partially in section, showing the expanded stent implanted in the artery wall after withdrawal of the balloon catheter.

FIG. 5 is a perspective view of the stent of FIG. 1, shown in a compressed or crimped state with the struts of each cylindrical ring overlapping the struts of each adjacent ring.

FIG. 6 is a perspective view of the stent of FIG. 1, shown in the as-machined state where the struts are closely spaced but not overlapping.

FIG. 7 is a perspective view of the stent of FIG. 1, shown in an expanded state.

FIG. 8 is an enlarged top plan view of one of the U-shaped portions which form the cylindrical rings of the stent of the present invention.

FIG. 9 is a side view of the U-shaped portion of FIG. 7.

DETAILED DESCRIPTION OF THE PREFERRED EMBODIMENTS

Figure 4A:
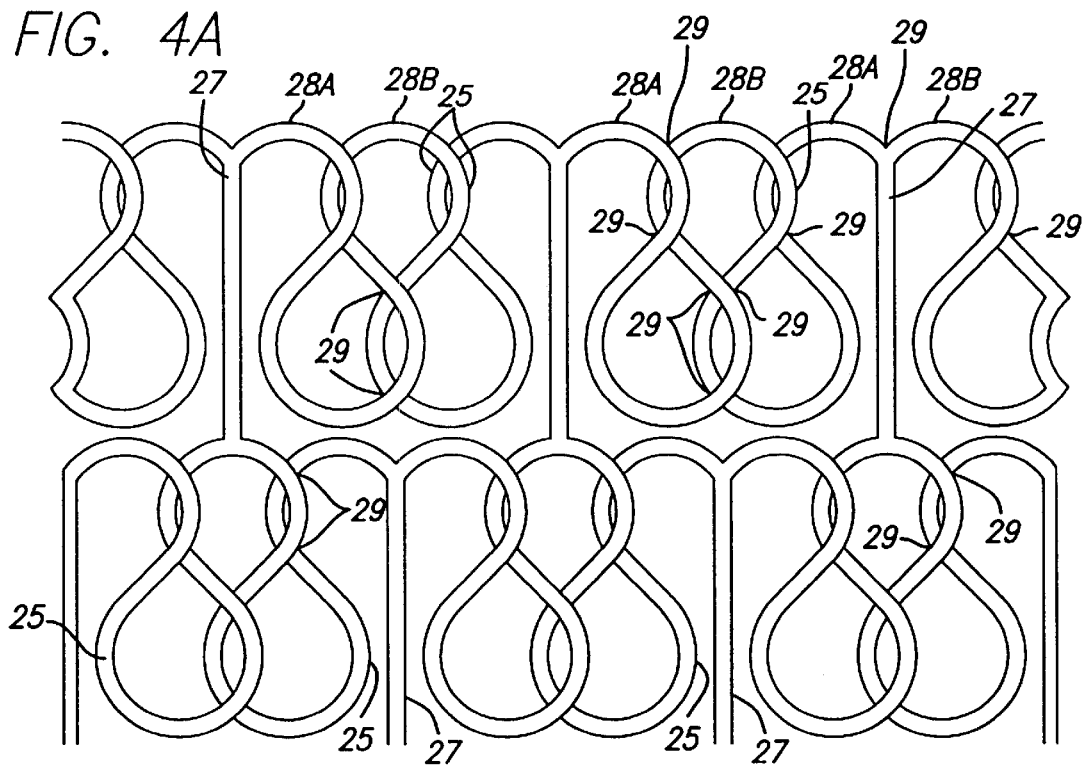
FIG. 4A is a plan view of a flattened section of one embodiment of the stent of the present invention in the delivery diameter configuration depicting overlapping struts.

The present invention stent improves on existing stents by providing a stent having a unique pattern with novel overlapping struts. The overlapping struts allow the stent to be crimped to a smaller delivery diameter than may be achieved with prior art stents. The present invention stent's reduced delivery diameter allows for the construction of reduced profile stent-delivery systems, which thereby allow for the successful stenting of smaller vessels than has heretofore been possible.

Referring to FIG. 1, the stent 10 of the present invention is shown mounted on a catheter 12 of the known rapid exchange configuration and having a lumen 14 and an inflation member 16. The stent and catheter are shown inside a lumen 22 of an arterial vessel 24. The stent is shown positioned across a small amount of arterial plaque 25 adhering to the wall 26 of the artery. The plaque 25 is the remainder of an arterial lesion which had been previously dilated or radically compressed against the walls of the artery or has been partially removed from the artery. Lesion dilation is typically accomplished by an angioplasty procedure, while lesion removal is typically accomplished by an atherectomy procedure. These and other procedures for the treatment of arterial lesions are well known to those skilled in the art.

With most lesion treatment procedures, the treated artery suffers a degree of trauma and in a certain percentage of cases may abruptly collapse or may slowly narrow over a period of time. To prevent either of these conditions, the treated artery is often fitted with a prosthetic device, such as the stent 10 of the present invention. The stent provides radial support for the treated vessel and thereby prevents collapse of the arterial vessel 24 and further provides scaffolding to prevent plaque prolapse within the lumen 22. The stent 10 may also be used to repair an arterial dissection, or an intimal flap, both of which are commonly found in the coronary arteries, peripheral arteries and other vessels. A low profile stent is desirable for the above mentioned treatments because a low profile stent may be more easily delivered to a lesion site, may be delivered to lesions within small vessels, and is less likely to abrade a lumen wall during delivery. Abrasion of lumen walls may cause particles of plaque or other material deposited within the lumen to break free from the lumen wall and migrate with the flow of blood as an embolic particle. Embolic particles may later lodge within a small blood vessel leading to full or partial occlusion of the vessel with adverse consequences to the patent.

With continued reference to FIG. 1, in a typical stent placement procedure, a guiding catheter (not shown) is percutaneously introduced into the cardiovascular system of a patient through the femoral arteries by means of a conventional Seldinger technique and advanced within a patient's vascular system until the distal end of the guiding catheter is positioned at a point proximal to the lesion site. A guide wire 20 and the stent-delivery catheter 12, are enclosed within a delivery sheath 18 (for use with a self-expanding stent), and are introduced through the guiding catheter with the guide wire sliding within the stent-delivery catheter. The guide wire is first advanced out of the guiding catheter into the arterial vessel 24 and is directed across the arterial lesion. The stent-delivery catheter 12 and protective sheath 18 are subsequently advanced over the previously advanced guide wire until the stent is properly positioned across the lesion.

Referring now to FIG. 2, once in position, the delivery sheath 18 (for use with a self-expanding stent) is withdrawn proximally and the dilation balloon 16 is inflated to a predetermined size to radially expand the stent 10 against the inside of the artery wall 26 and thereby implant the stent 10 within the lumen 22 of the artery. The balloon is then deflated to a small profile so that the stent-delivery catheter 12 may be withdrawn from the patient's vasculature and blood flow resumed through the artery.

Since the stent 10 typically is formed from an elongated tubular member (it may be formed flat and rolled into a cylinder or tube), the rings and links of the stent are relatively flat in transverse cross-section, thus after implantation into the artery 22 as shown in FIG. 3, minimal interference with blood flow occurs. Eventually the stent becomes covered with endothelial cell growth which further minimizes blood flow interference. As should be appreciated by those skilled in the art, while the above-described procedure is typical, it is not the only method used in placing stents.

Figure 4B:
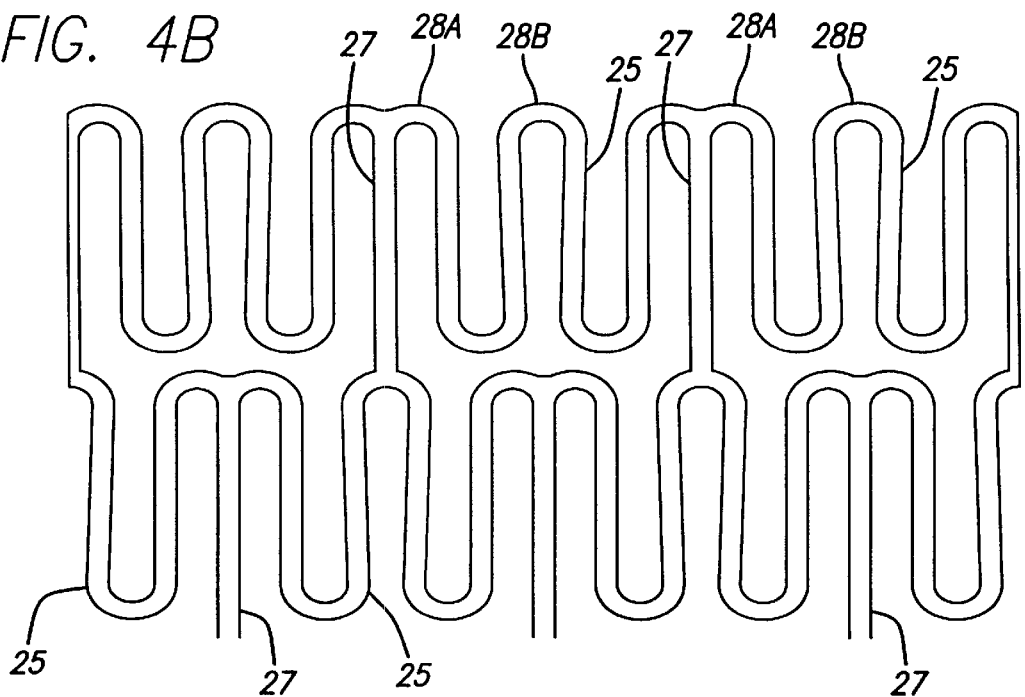
FIG. 4B is the stent of FIG. 4A in the expanded configuration where the struts no longer overlap.

In one embodiment, as shown in FIGS. 4A and 4B, the stent 10 has a number of curved struts 25 and straight struts 27. There are numerous stent patterns that are well known and that have both curved and straight struts arranged in various patterns. Thus, FIGS. 4A and 4B are merely representative of a strut pattern that has curved and straight struts. The invention, however, applies to any combination of all curved, all straight, or curved and straight patterns. As shown in FIG. 4A, in the smaller delivery diameter, the curved struts are overlapping at multiple points 29. The overlapping points 29 create an inner diameter portion 28A and an outer diameter portion 28B. As shown in FIG. 4B, when the stent is expanded to the expanded implanted diameter, the curved struts 25 are no longer overlapping with each other. Again, not all of the curved or straight struts overlap, and the number and positioning of the overlaps may vary with specific applications. FIGS. 4A and 4B depict a flattened stent for ease of illustration and it is well known in the art that stents preferably have a cylindrical configuration (and which also may be tapered).

Typically, the stent 10 is laser cut from a solid tube. Thus, the stent does not possess discreet individual components. However, for the purposes of description it is beneficial to refer to the stent as being composed of cylindrical rings and connecting links. In one embodiment, it is also beneficial to refer to the individual rings, when viewed in isolation, as being composed of alternating U-shaped portions. Alternatively, the rings may be visualized as being composed of alternating peak and valley portions.

Referring now to FIGS. 5, 6, and 7, in one embodiment, the stent 10 is made up of a plurality of cylindrical rings 30 which extend circumferentially around the stent, and of longitudinal connecting links 31, where at least one connecting link connects each adjacent ring. The stent has an initial delivery diameter 32 as shown in FIG. 5, and an as machined diameter 34 as shown in FIG. 6. The stent further has an expanded diameter as shown in FIG. 7. Each cylindrical ring 30 has a cylindrical ring proximal end 36 and a cylindrical ring distal end 38. Each cylindrical ring 30 defines a cylindrical plane 40 which is a plane defined by the proximal and distal ends of the ring, 36 and 38, and the circumferential extent as the cylindrical ring travels circumferentially around the cylinder. Each cylindrical ring includes a cylindrical outer wall surface 42 which defines the outermost surface of the stent, and a cylindrical inner wall surface 44 which defines the innermost surface of the stent. The cylindrical plane 40 follows the cylindrical outer wall surface. When viewed in isolation, as is shown by the cutaway portions of FIGS. 5, 6, and 7, each cylindrical ring is composed of a plurality of stylized U-shaped portions 46, each of which includes a closed apex 45 and an open end 47 (FIG. 8). Alternatively, the cylindrical rings may be described as comprising a plurality of alternating peaks 45 and valleys 47.

Referring now to FIGS. 8 and 9, a single U-shaped portion 46, as it would appear when the stent 10 is compressed or crimped to its initial delivery diameter, is depicted. The U-shaped element 46 includes a pair of generally S-shaped struts 48, which have respective first ends 49 and second ends 50. The first ends of the struts are joined to form the apex or peak 45 of the U-shaped portion. The second ends curve outwardly to form the open end or valley 47 of the U-shaped portion. Each S-shaped strut is further comprised of an upper portion 52 and a lower portion 54. Joining the upper and lower portions is a stepped transition portion 56. The stepped transition portion allows the lower portion of each strut to slide underneath the upper portion of each preceding, nested U-shaped element in the preceding, nested cylindrical ring 30. Therefore, when the stent 10 is crimped or compressed to its initial delivery diameter, the lower portions of the struts in each cylindrical ring slide underneath the upper portions of the struts in the preceding nested cylindrical ring, thereby creating a pattern of overlapping struts which allows the stent to be compressed to a smaller diameter than would be possible if the struts were all on the same cylindrical plane.

It should be noted that the struts 48 need not be S-shaped, but rather may be composed of other irregular curved segments or of angled straight segments. What is important is that the struts have a transition region 56 which allows the struts of one cylindrical ring to overlap the struts of an adjacent cylindrical ring.

Due to its overlapping strut configuration, balloon expandable embodiments of the stent 10 of the present invention have essentially three static diameters. As manufactured, the stent has a diameter slightly larger than it has when compressed or crimped, i.e., the struts 48 are closely spaced but are not overlapping (FIG. 6). In the initial delivery diameter, the struts are overlapping, i.e., the stent has been compressed or crimped and the lower portions 54 of the struts have slid underneath the upper portions 52 of the struts on each adjacent cylindrical ring 30 (FIG. 5). In the expanded state, the struts are no longer overlapping, but rather are now substantially separated as the stent has been plastically deformed to a comparatively large diameter with respect to the as manufactured diameter or initial delivery diameter (FIG. 7).

Self-expanding embodiments of the stent 10 do not have an intermediate diameter between the initial delivery diameter and the expanded diameter. With self-expanding embodiments, the as manufactured diameter is substantially equivalent to the stent's expanded or deployed diameter. The initial delivery diameter is essentially the same as that of balloon expandable versions, however, the self-expanding embodiments are typically held at their compressed, initial delivery diameter by means of a delivery sheath.

As will be appreciated, when crimped about the inflation balloon 16, the relative motion of the struts 48 will tend to engage or pinch the balloon material, thereby more securely affixing the stent 10 to the balloon. In addition, the overlapping strut pattern provides the stent with a radial depth that is about twice the strut thickness. The increased radial thickness allows the balloon to protrude into the gaps between the struts which also tends to improve retention of the stent on the balloon.

Figure 10:
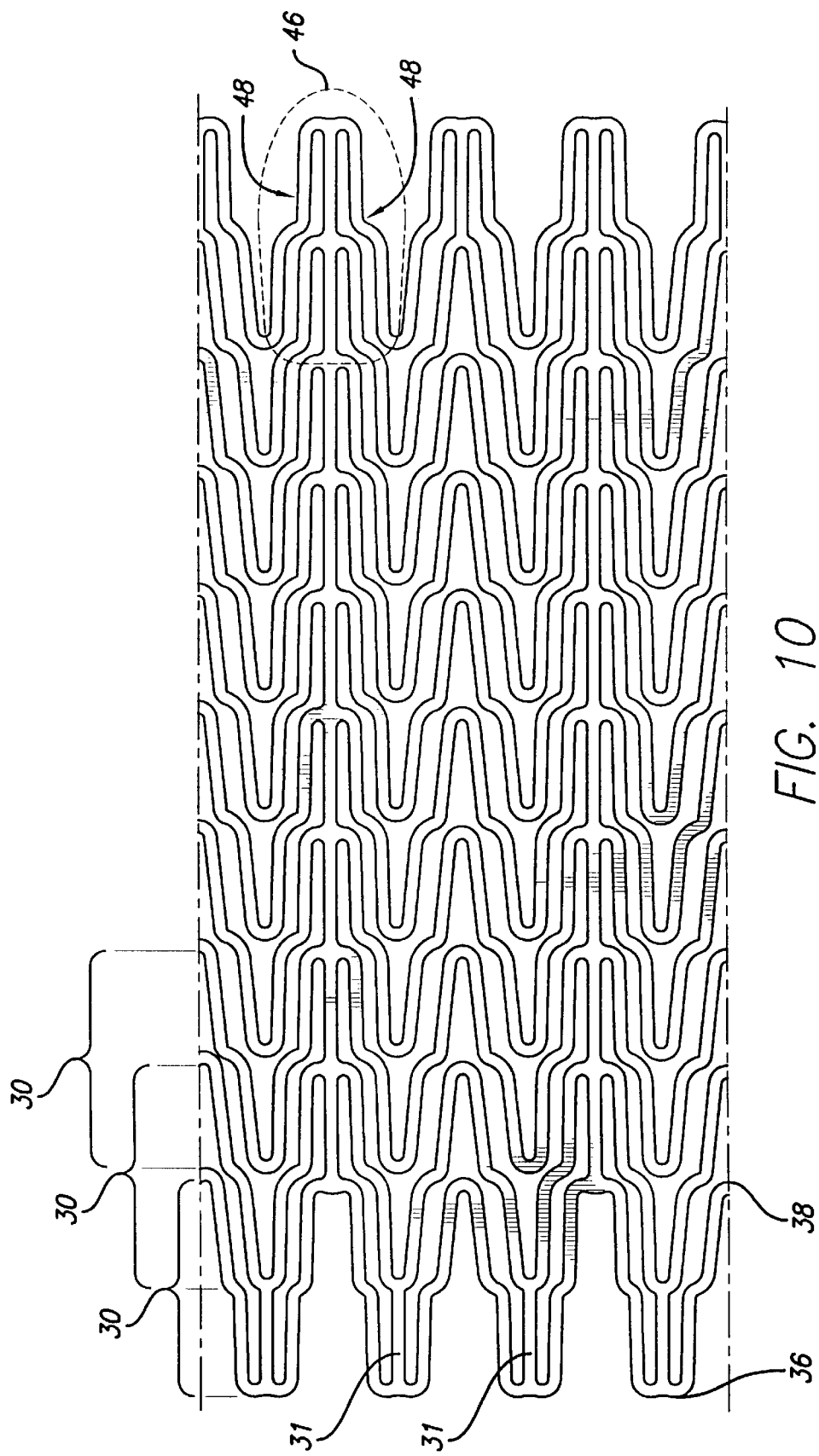
FIG. 10 is a plan view of a flattened section of one embodiment of the stent of the present invention, shown in the as machined state where the struts are closely spaced but not overlapping.

Referring now to FIG. 10, for the purpose of illustration only, the stent 10 is shown in its as manufactured state as a flat pattern so that the pattern of rings 30 and links 31 may be more clearly viewed. In the as manufactured state, the U-shaped portions 46 and the struts 48 are relatively straight and angular in appearance in contrast to the generally curved appearance these portions have in their compressed initial delivery state. In the exemplary embodiment shown in FIG. 10, each cylindrical ring is connected to each adjacent ring by three rows of longitudinal connecting links which are equally spaced at 120 degree intervals around the circumference of the stent. In alternative embodiments, the connecting links may be radially offset from one adjacent ring to the next.

Again, it is to be emphasized that the above described rings, U-shaped portions, struts, and connecting links are for purposes of clarity of description only. The stent 10 is machined as a unitary structure and therefore does not actually contain any discrete components.

Figure 11A:
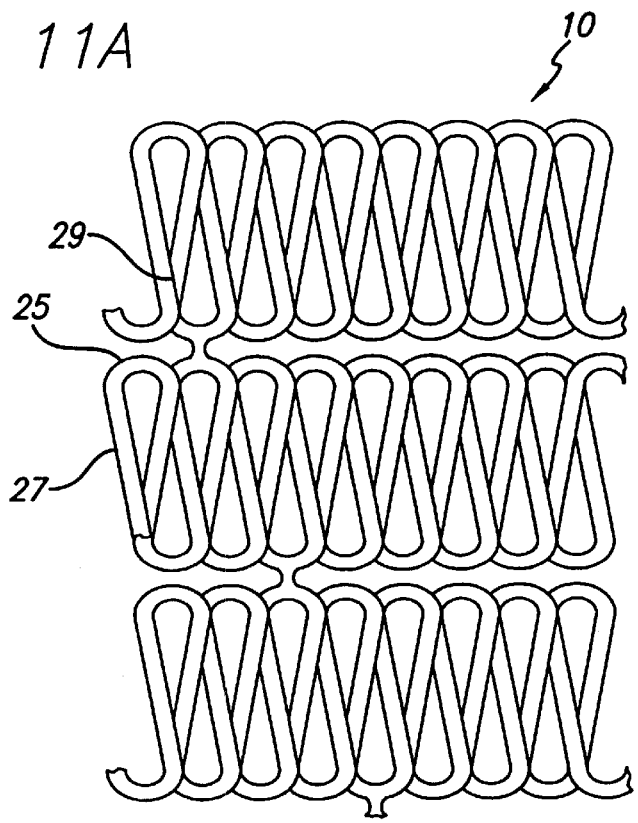
FIG. 11A is a plan view of a flattened section of one embodiment of the stent of the present invention where the struts are overlapping in the delivery diameter configuration.
Figure 11B:
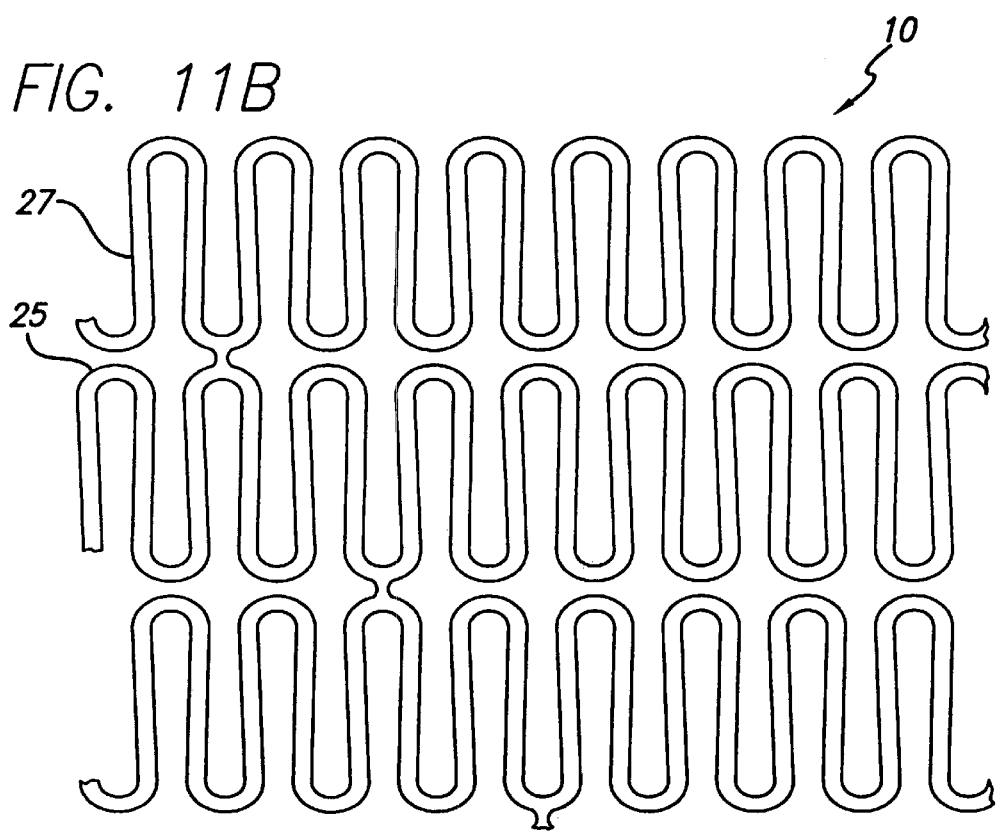
FIG. 11B is the stent of FIG. 11A in the expanded configuration where the struts are not overlapping.
Figure 12A:
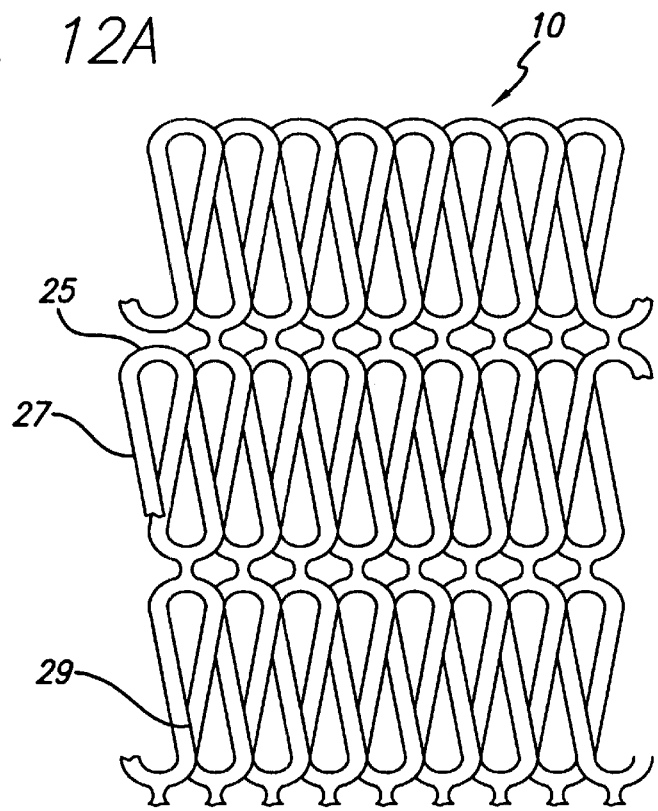
FIG. 12A is a plan view of a flattened section of one embodiment of the tent of the present invention where the struts are overlapping in the delivery diameter configuration.
Figure 12B:
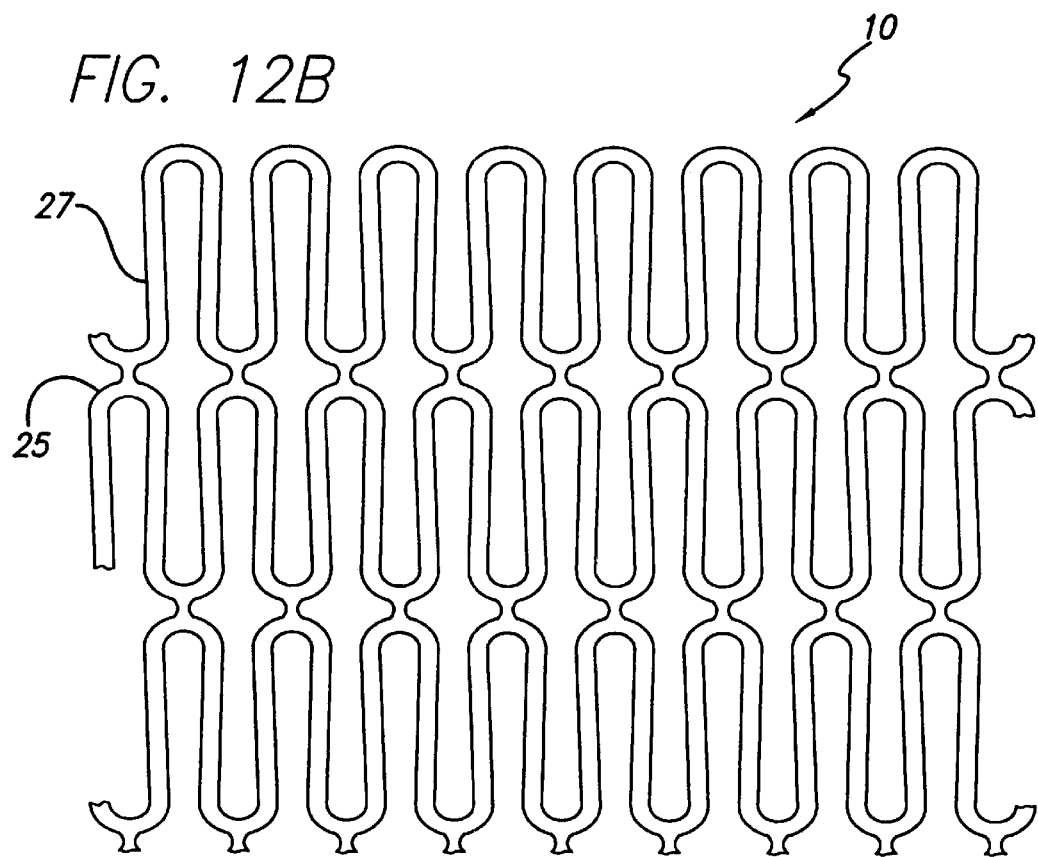
FIG. 12B is the stent of FIG. 12A in the expanded configuration where the struts are not overlapping.
Figure 13A:
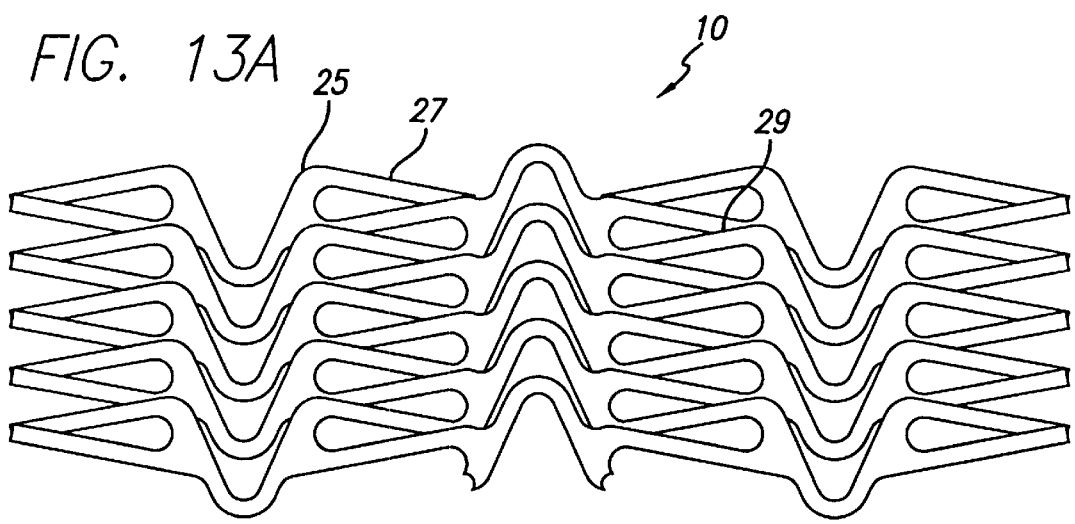
FIG. 13A is a plan view of a flattened section of one embodiment of the stent of the present invention where the struts are overlapping in the delivery diameter configuration.
Figure 13B:
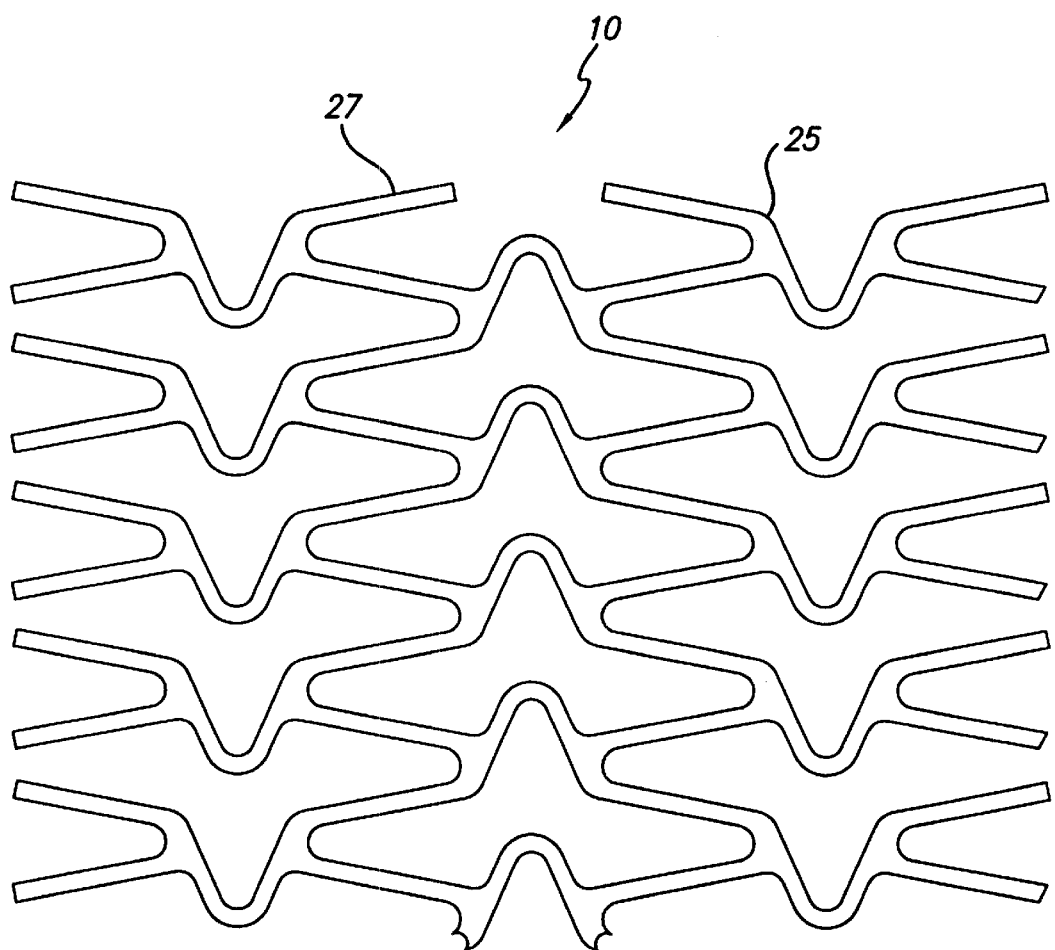
FIG. 13B is the stent of FIG. 13A in the expanded configuration where the struts are not overlapping.
Figure 14A:
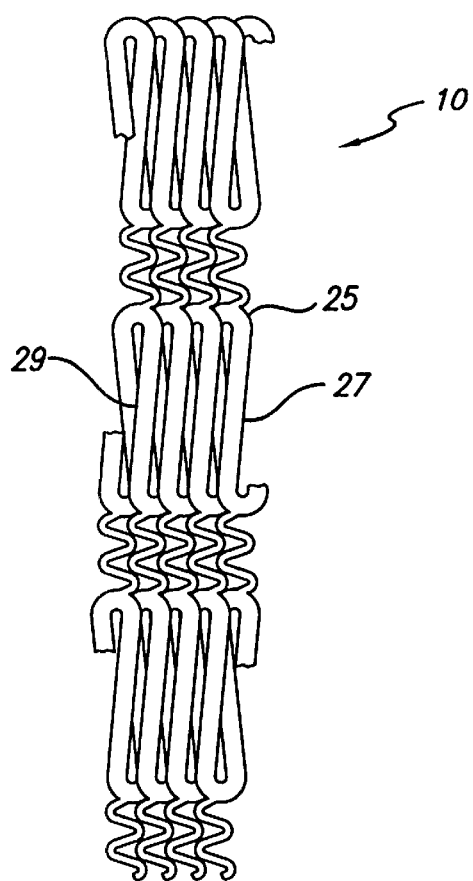
FIG. 14A is a plan view of a flattened section of one embodiment of the stent of the present invention where the struts are overlapping in the delivery diameter configuration.
Figure 14B:
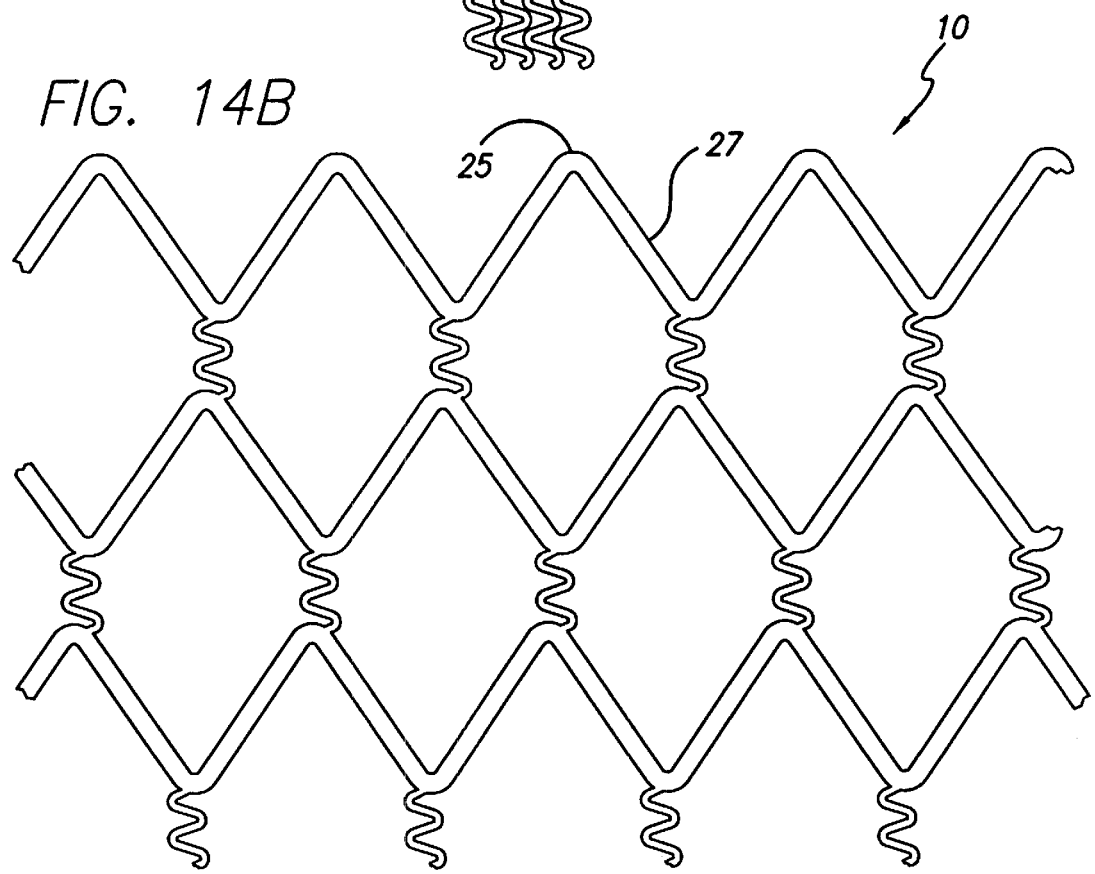
FIG. 14B is the stent of FIG. 14A in the expanded configuration where the struts are not overlapping.
Figure 15A:
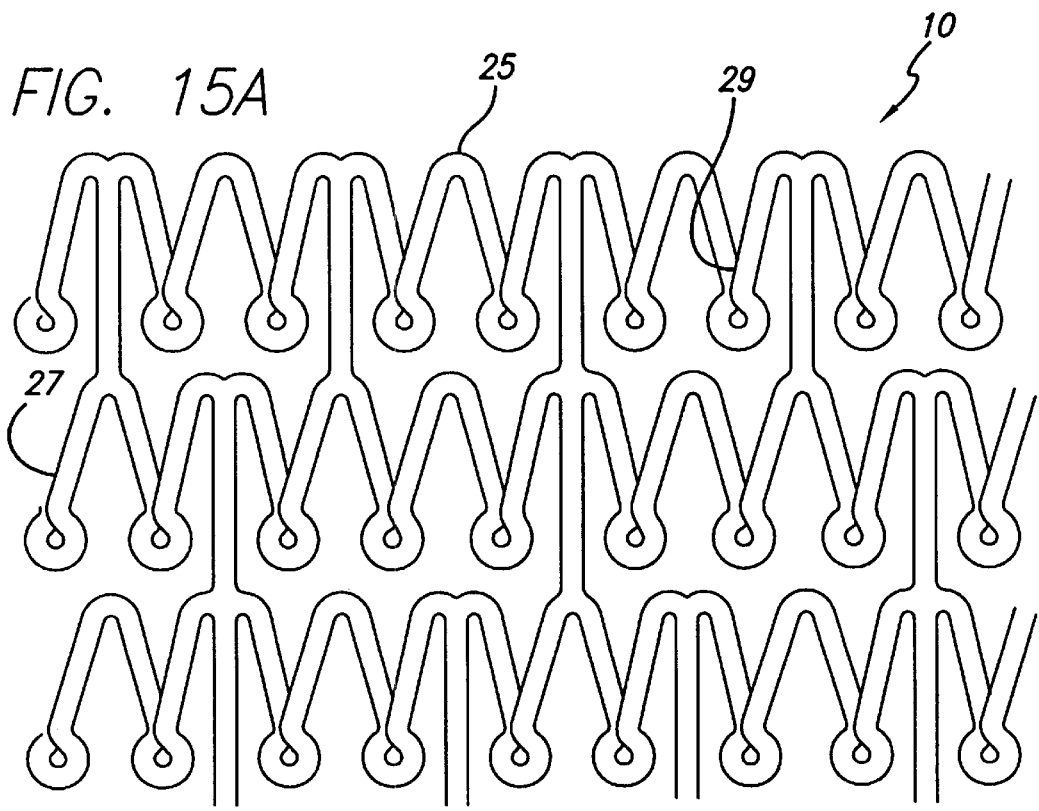
FIG. 15A is a plan view of a flattened section of one embodiment of the stent of the present invention where the struts are overlapping in the delivery diameter configuration.
Figure 15B:
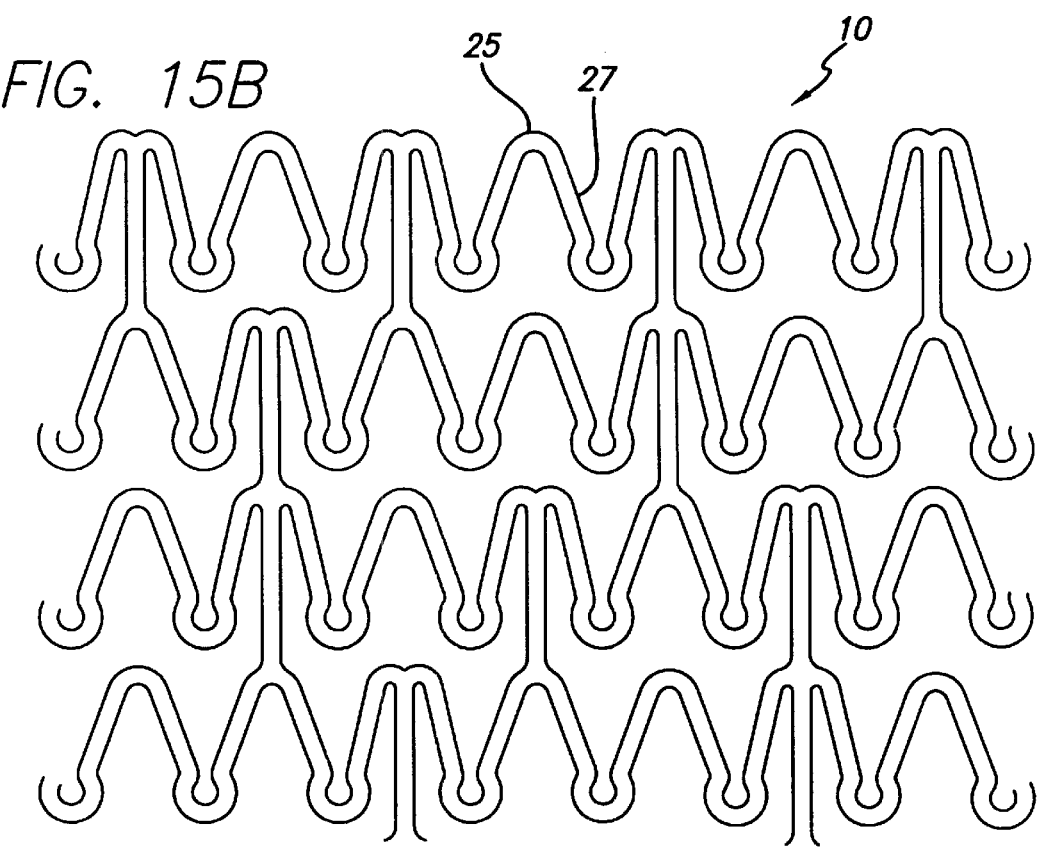
FIG. 15B is the stent of FIG. 15A in the expanded configuration where the struts are not overlapping.

Alternative embodiments of the stent of the present invention are shown in FIGS. 11A and 11B, 12A and 12B, 13A and 13B, 14A and 14B, 15A and 15B. The stents shown in FIGS. 11A–15B represent stent patterns that are well known and which are adapted to incorporate the overlap features of the present invention as described. Importantly, the struts of these embodiments may overlap in any manner to achieve the desired low profile delivery diameter, high gripping force on the catheter, and enhanced expanded diameter. The stent shown in FIGS. 11A and 11B is sold under the tradename GFX and is manufactured by AVE Medtronic of Santa Rosa, Calif. The stent shown in FIGS. 12A and 12B is sold under the tradename AVE S670 and is manufactured by AVE Medtronic of Santa Rosa, Calif. The stent shown in FIGS. 13A and 13B is sold under the tradename NIR by Boston Scientific Corporation of Natick, Mass. The stent shown in FIGS. 14A and 14B is sold under the tradename BX VELOCITY and is manufactured by Cordis Corporation, a division of Johnson & Johnson Company, Warren, N.J. The stent shown in FIGS. 15A and 15B is sold under the tradename DUET and is manufactured by Advanced Cardiovascular Systems, Inc. of Santa Clara, Calif.

The stent 10 may be produced by several methods including electro-discharge machining and chemical etching. However, the preferred method is to laser cut a thin-walled tubular member, such as a hypotube. In this procedure, a computer controlled laser cuts away portions of the hypotube following a pre-programmed template to form the desired strut pattern. Methods and equipment for laser machining small diameter tubing are known in the art.

The laser machining process leaves a thin heat effected zone around the pattern cut in the drawn tube and a resulting surface finish that is somewhat coarse and unsuitable for implantation in living tissue. The surface roughness of stents in the "as machined" condition is on the order of about 50–100 microns, while stents suitable for implantation within a blood vessel typically require a surface roughness of about 0.2 to 0.05 microns.

To achieve the required surface finish, stents are typically descaled and electro-polished. One method of descaling involves immersing the stents in an alkaline cleaner and ultrasonically agitating the stents for a selected period of time. Another method involves bead blasting stents with fine glass beads. There are other procedures for descaling are well known to those skilled in the art.

The principles of electro-polishing are also known in the art. Typically, an item to be electro-polished is immersed in an electrolyte which comprises an aqueous acidic solution. The item to be polished is made a positive electrode (anode) and a negative electrode (cathode) is placed in close proximity to the anode. The anode and cathode are connected to a source of electric potential difference with the electrolyte completing the circuit between anode and cathode. Upon the passage of electric current through the electrolyte, metal is dissolved from the anode surface with protrusions being dissolved faster than depressions, thereby producing a smooth surface. The rate of material removal in an electro-polishing process is primarily a function of the electrolyte chosen and the current density in the electrolyte fluid.

Typically, with stainless steel stents, a final step in the electro-polishing process involves passivation of the newly polished surface. After removal from the electrolyte solution and rinsing with water, residual anions of the acid used in the electrolyte remain in contact with the polished surface. The presence of such surface anions leads to deterioration of the newly polished surface when the residual anions come into contact with calcium and magnesium ions which are commonly found in non-deionized water (ordinary tap water). To prevent surface deterioration, newly polished stents are immersed in a passivation bath which typically consists of a solution of nitric acid, deionized water, and sodium dichromate. The passivation bath neutralizes the residual anions and leaves a protective, corrosion resistant, strongly adherent, transparent, chromium dioxide coating on the newly polished surface.

With nickel-titanium alloy stents, however, the passivation step is generally not required. Nickel-titanium alloys tend to form a titanium oxide rich surface layer during initial heat treatment of the alloy which renders the alloy relatively impervious to the corrosive effects of any residual anions that may be left on the stent surface after electro-polishing.

The tubing used to make the stent 10 may be made of any bio-compatible spring steel or shape memory alloy. The 300 series stainless steel alloys are well suited to this application with type 316L stainless steel per ASTM F138-92 or ASTM F139-92 grade 2 being preferred. Of the shape memory or super-elastic alloys, Nitinol, a 55% nickel—45% titanium alloy is preferred. Other shape memory alloys such as Ni—Ti—X (X being V, Co, Cu, Fe) ternary alloys, Cu—Al—Ni ternary alloys and Cu—Zn—Al ternary alloys are also suitable.

Typically, suitably sized tubing for making the stent 10 will have an outside diameter of about 0.020–0.060 inches, with a wall thickness of about 0.003–0.006 inches. However, tubing size will vary depending upon the application. It is preferred that the stent be machined from seamless tubing. However, tubing formed by rolling flat, sheet stock into a cylinder with welded longitudinal edges is also suitable, as is rolled sheet stock which has been drawn through a circular die.

It will be appreciated that a new stent having an overlapping strut pattern has been presented. The overlapping strut pattern allows the stent to crimped to a smaller initial delivery profile than has heretofore been possible. The lower profile allows physicians to reach and treat lesions in smaller and more tortuous vessels than may be treated with conventional stents. In addition, the overlapping strut pattern allows balloon material to be caught between the sliding struts and thereby improves stent security on an inflation balloon.

While only the presently preferred embodiments have been described in detail, as will be apparent to those skilled in the art, modifications and improvements may be made to the device and method disclosed herein without departing from the scope of the invention. Accordingly, it is not intended that the invention be limited, except as by the appended claims.

What is claimed:

1. An intravascular stent for use in a body lumen, comprising:
    an elongated tubular body having a plurality of struts forming a stent pattern;
    the tubular member having a first diameter for navigating the body lumen and a second expanded diameter for implanting in the body lumen; and
    at least some of the struts are overlapping at multiple points and some of the struts are non-overlapping when the tubular member is in the first diameter and the overlapping struts expand and become non-overlapping struts in the second expanded diameter configuration.

2. The stent of claim 1, wherein the stent pattern has a plurality of cylindrical rings that are interconnected.

3. The stent of claim 2, wherein the cylindrical rings are connected by at least one connector member.

4. The stent of claim 3, wherein the at least on connector member is a link.

5. The stent of claim 2, wherein at least some of the cylindrical rings have overlapping struts.

6. The stent of claim 3, wherein the at least one connector member has struts which overlap the cylindrical ring struts.

7. The stent of claim 1, wherein the overlapping struts define an inner diameter portion and an outer diameter portion.

8. An intravascular stent for use in a body lumen, comprising:
    a plurality of nested cylindrical rings having an initial delivery diameter and an expanded deployed diameter, rings being formed from a plurality of alternating U-shaped portions, each of the plurality of U-shaped portions lying in more than one cylindrical plane;
    the U-shaped portions of each cylindrical ring overlap the U-shaped portions of each adjacent cylindrical ring when the cylindrical rings are in the initial delivery diameter;
    each cylindrical ring having a proximal end and a distal end a cylindrical wall extending circumferentially between the proximal end and the distal end of the cylindrical ring; and
    the cylindrical rings being interconnected to from the stent, wherein at least one connecting link attaches each cylindrical ring to an adjacent cylindrical ring.

9. The stent of claim 8, wherein each U-shaped element is formed from struts, the struts having first ends and second ends and being joined at the first ends to form an apex, and curving outwardly therefrom to form an open end of the U-shaped portion.

10. The stent of claim 9, wherein each strut has a stepped transition portion which divides each strut into an upper portion and a lower portion.

11. The stent of claim 10, wherein the lower portions of the struts in each cylindrical ring slide underneath the upper portions of the struts in an adjacent cylindrical ring, when the stent is compressed to the delivery diameter.

12. The stent of claim 9, wherein each strut has a generally S-shaped configuration.

13. The stent of claim 9, wherein the apex of each U-shaped element in each cylindrical ring is circumferentially offset from the apex of each U-shaped element in each adjacent ring.

14. The stent of claim 9, wherein the nested cylindrical rings are nested such that the apexes of each ring are centered approximately midway within the U-shaped portions of each adjacent ring.

15. The stent of claim 8, wherein the stent is formed from a tube.

16. The stent of claim 8, wherein the stent is formed from a metal alloy.

17. The stent of claim 8, wherein the stent is formed from stainless steel.

18. The stent of claim 8, wherein the stent is formed from a shape memory alloy.

19. The stent of claim 8, wherein the stent is formed from a superelastic alloy.

20. The stent of claim 8, wherein the stent is formed from a polymer.

21. A stent for use in a body lumen, comprising:

a plurality of nested cylindrical rings interconnected to form the stent, each cylindrical ring having an initial delivery diameter and an expanded deployed diameter;

each cylindrical ring having a plurality of peaks and valleys, the valleys of one cylindrical ring being circumferentially offset from the valleys of an adjacent cylindrical ring and the peaks of each cylindrical ring being in a different cylindrical plane than the valleys of the same cylindrical ring, wherein the valleys of one cylindrical ring overlap the peaks of an adjacent cylindrical ring when the cylindrical rings are in the delivery diameter; and at least one connecting link attaching each cylindrical ring to an adjacent cylindrical ring, the at least one connecting link being positioned substantially within one of the valleys and attaching the valley to an adjacent peak.

22. The stent of claim 21, wherein the cylindrical rings are nested such that the peaks of one cylindrical ring are centered approximately midway within the valleys of an adjacent cylindrical ring.

23. The stent of claim 21, wherein each peak and valley is formed from struts, the struts having first ends and second ends and being joined at the first ends to form a peak and being separated at the second ends to form a valley therebetween.

24. The stent of claim 23, wherein each strut has a stepped transition portion which divides each strut into an upper portion and a lower portion.

25. The stent of claim 24, wherein the lower portions of the struts in each cylindrical ring slide underneath the upper portions of the struts in an adjacent cylindrical ring, when the stent is compressed to the delivery diameter.

26. The stent of claim 23, wherein each strut has a generally S-shaped configuration.

27. The stent of claim 21, wherein the stent is formed from a tube.

28. The stent of claim 21, wherein the stent is formed from a metal alloy.

29. The stent of claim 21, wherein the stent is formed from stainless steel.

30. The stent of claim 21, wherein the stent is formed from a shape memory alloy.

31. The stent of claim 21, wherein the stent is formed from a superelastic alloy.

32. The stent of claim 21, wherein the stent is formed from a polymer.

33. A stent for use in a body lumen, comprising:

a plurality of nested cylindrical rings interconnected to form the stent, each cylindrical ring having an initial delivery diameter and an expanded deployed diameter;

each cylindrical ring having a plurality of peaks and valleys;

means for causing the valleys of each cylindrical ring to overlap the peaks of each adjacent cylindrical ring when the stent is compressed to the initial delivery diameter;

means for causing the valleys of each cylindrical ring to no longer overlap the peaks of each adjacent cylindrical ring when the stent is in the expanded deployed diameter; and means for connecting each cylindrical ring to an adjacent cylindrical ring.

* * * * *

UNITED STATES PATENT AND TRADEMARK OFFICE
CERTIFICATE OF CORRECTION

PATENT NO.    : 6,579,310 B1
DATED         : June 17, 2003
INVENTOR(S)   : Daniel L. Cox et al.

It is certified that error appears in the above-identified patent and that said Letters Patent is hereby corrected as shown below:

Column 5,
Line 26, after "Referring", insert -- now --.

Column 10,
Line 36, change "at least on", to read -- at least one --.

Signed and Sealed this

Fourteenth Day of October, 2003

JAMES E. ROGAN
*Director of the United States Patent and Trademark Office*